United States Patent
Stoer et al.

(10) Patent No.: US 12,390,413 B2
(45) Date of Patent: Aug. 19, 2025

(54) BIOBASED PEARLESCENT WAXES

(71) Applicant: BASF SE, Ludwigshafen (DE)

(72) Inventors: Claudia Stoer, Monheim (DE); Claus Nieendick, Düsseldorf-Holthausen (DE); Markus Dierker, Düsseldorf (DE); Ansgar Behler, Düsseldorf-Holthausen (DE); Sybille Cornelsen, Monheim (DE); Werner Mauer, Düsseldorf-Holthausen (DE)

(73) Assignee: BASF SE, Ludwigshafen (DE)

( * ) Notice: Subject to any disclaimer, the term of this patent is extended or adjusted under 35 U.S.C. 154(b) by 766 days.

(21) Appl. No.: 17/430,497

(22) PCT Filed: Feb. 18, 2020

(86) PCT No.: PCT/EP2020/054236
§ 371 (c)(1),
(2) Date: Aug. 12, 2021

(87) PCT Pub. No.: WO2020/173761
PCT Pub. Date: Sep. 3, 2020

(65) Prior Publication Data
US 2022/0133620 A1  May 5, 2022

(30) Foreign Application Priority Data

Feb. 27, 2019 (EP) .................................. 19159688

(51) Int. Cl.
*A61K 8/92* (2006.01)
*A61Q 5/02* (2006.01)
*A61Q 19/10* (2006.01)

(52) U.S. Cl.
CPC .................. *A61K 8/92* (2013.01); *A61Q 5/02* (2013.01); *A61Q 19/10* (2013.01); *A61K 2800/436* (2013.01)

(58) Field of Classification Search
CPC ...... A61K 8/92; A61K 2800/436; A61Q 5/02; A61Q 19/10
See application file for complete search history.

(56) References Cited

U.S. PATENT DOCUMENTS

| | | | |
|---|---|---|---|
| 5,747,435 A | 5/1998 | Patel | |
| 5,888,487 A * | 3/1999 | Baumoeller | A61Q 5/02 424/501 |
| 8,183,298 B2 | 5/2012 | Issberner et al. | |
| 8,436,046 B2 | 5/2013 | Fenyvesi et al. | |
| 9,221,971 B2 | 12/2015 | Tammaji et al. | |
| 2005/0143277 A1 * | 6/2005 | Dufay | C11D 1/94 510/424 |
| 2013/0190217 A1 * | 7/2013 | Lammle | C10M 105/38 560/204 |
| 2014/0357808 A1 | 12/2014 | Hess et al. | |
| 2015/0209257 A1 | 7/2015 | Gebert et al. | |
| 2015/0335550 A1 | 11/2015 | Koshti et al. | |
| 2017/0172882 A1 * | 6/2017 | Neuba | A61K 8/22 |
| 2018/0037696 A1 | 2/2018 | Mehta | |

FOREIGN PATENT DOCUMENTS

| | | | |
|---|---|---|---|
| CA | 2762589 A1 * | 6/2013 | ............ A45D 34/00 |
| CN | 1196675 A | 10/1998 | |
| CN | 1937991 A | 3/2007 | |
| CN | 101525416 A | 9/2009 | |
| CN | 104387568 A | 3/2015 | |
| DE | 19511572 A1 | 10/1996 | |
| EP | 0376083 A2 | 7/1990 | |
| EP | 1830798 B1 | 12/2014 | |
| FR | 2252840 A1 | 6/1975 | |
| GB | 1494915 A | 12/1977 | |
| JP | 2003-105380 A | 4/2003 | |
| JP | 2013-530300 A | 7/2013 | |
| JP | 2014-055138 A | 3/2014 | |
| JP | 2015-160911 A | 9/2015 | |
| KR | 10-0145316 B1 | 7/1998 | |
| SG | 146386 | 11/2011 | |
| WO | WO-90/07323 A2 | 7/1990 | |
| WO | WO-98/38973 A1 | 9/1998 | |
| WO | WO-03/011246 A1 | 2/2003 | |
| WO | WO-2003/066796 A1 | 8/2003 | |
| WO | WO-03083031 A1 * | 10/2003 | ............ A61K 8/585 |
| WO | WO-03/104318 A1 | 12/2003 | |
| WO | WO-2007/095255 A2 | 8/2007 | |
| WO | WO-2008/057220 A2 | 5/2008 | |
| WO | WO-2008/057317 A1 | 5/2008 | |
| WO | WO-2012/177886 A2 | 12/2012 | |
| WO | WO-2016198848 A1 * | 12/2016 | ........... A61K 31/194 |
| WO | WO-2018/089600 A1 | 5/2018 | |

(Continued)

OTHER PUBLICATIONS

Machine translation of WO2017098149A9 (Year: 2017).*
Carbon 14 dating; https://www.google.com/search q=carbon+14+dating&rlz=1C1GCEA_enUS1059US1059&oq=carbon+14+da&gs_lcrp=EgZjaHJvbWUqBwgAEAAYgAQyBwgAEAAYgAQyBggBE EUYOTIHCAIQABiABDIHCAMQABiABDIHCAQQABiABDIH CAUQABiABDIHCAYQABiABDIHCAcQABiABDIHCAgQABi ABDIHCAkQABiABKgCALACAA&sourceid=chrome&ie=UTF-8; 2024 (Year: 2024).*
Tracking fossil fuel emissions with carbon-14; https://research.noaa.gov/2020/06/01/fingerprinting-fossil-fuel-emissions-with-carbon-14/#:~:text=Carbon%2D14%2C%20or%2014C,completely%20devoid%20of%2014C. accessed Jun. 2024 (Year: 2020).*

(Continued)

*Primary Examiner* — Robert A Wax
*Assistant Examiner* — John W Lippert, III
(74) *Attorney, Agent, or Firm* — Faegre Drinker Biddle & Reath LLP

(57) ABSTRACT

The invention relates to biobased waxy esters which in particular in the form of wax dispersions bring about cloudiness and/or pearlescence in cosmetic cleansers. The invention further provides the use of the waxes in cosmetic compositions, the production thereof and the cosmetic compositions themselves.

22 Claims, No Drawings

(56) References Cited

FOREIGN PATENT DOCUMENTS

| WO | WO-2017098149 A9 * | 5/2018 | ........... B27K 3/0221 |
|---|---|---|---|
| WO | WO-2019/123468 A2 | 6/2019 | |
| WO | WO-2020/173761 A1 | 9/2020 | |

OTHER PUBLICATIONS

What is ethylene glycol?; https://byjus.com/chemistry/ethylene-glycol/#:~:text=Ethylene%20glycol%20has%20been%20synthesized,of%20naptha%20from%20petroleum%20refining. site accessed Jun. 2024 (Year: 2020).*

European Search Report for EP Patent Application No. 19159688.1, Issued on Jul. 3, 2019, 3 pages.

Lochhead, et al., "Encyclopedia of polymers and thickeners for cosmetics", Cosmetics and toiletries, vol. 108, May 1993, pp. 95-135.

"Feste Sekundärbrennstoffe—Verfahren zur Bestimmung des Gehaltes an Biomasse; Deutsche Fassung EN 15440:2011 (Solid recovered fuels—Methods for the determination of biomass content; German version EN 15440:2011)", retrieved on Dec. 13, 2023, pp. 1-2. URL: https://www.beuth.de/de/norm/din-en-15440/134729684.

"Katalog der firma KLK Oleo (Catalogue of the company KLK Oleo)", Sep. 2015, 18 Pages.

"Safety Assessment of Monoalkylglycol Dialkyl Acid Esters as Used in Cosmetics", Scientific Literature Review for Public Comment, Cosmetic Ingredient Review, Oct. 6, 2016, 36 Pages.

Bolzinger, et al., "Effects of surfactants on crystallization of ethylene glycol distearate in oil-in-water emulsion", Colloids and Surfaces A: Physicochemical and Engineering Aspects, vol. 299, Issue 1-3, May 15, 2007, pp. 93-100.

Chang, "Vegetable oil as organic solvent for wastewater treatment in liquid membrane processes", Desalination and Water Treatment, vol. 52, Issue 1-3, Jan. 2014, pp. 88-101.

Crombie, "Cold pearl surfactant-based blends", International journal of cosmetic science, vol. 19, Issue 5, Oct. 1997, pp. 205-214.

Ivanciuc, et al., "Estimation of the Liquid Viscosity of Organic Compounds with a Quantitative Structure-Property Model", Journal of chemical information and computer sciences, vol. 39, Issue 3, Mar. 31, 1999, pp. 515-524.

Jou, et al., "Biogenic fraction in the synthesis of polyethylene terephthalate", International Journal of Mass Spectrometry, vol. 388, Sep. 15, 2015, pp. 65-68.

Lee, et al., "A comprehensive metabolic map for production of bio-based chemicals", Nature Catalysis, vol. 2, Issue 1, Jan. 14, 2019, pp. 18-33.

Nacharbeitung des Beispiels B des Streitpatents EP 3930670 B1 (Reworking of Example B of Patent in Suit EP 3930670 B1), 4 Pages.

Wayback Machine: India Glycols—MEG/DEG/TEG, retrieved on Nov. 9, 2023, pp. 1-2. URL: https://web.archive.org/web/20111206224207/https://www.indiaglycols.com/product_groups/monoethylene_glycol.htm.

Yue, et al., "Ethylene glycol: properties, synthesis, and applications", Chemical Society Reviews, vol. 41, Issue 11, Apr. 10, 2012, pp. 4218-4244.

International Application No. PCT/EP2020/054236, International Search Report, mailed May 18, 2020.

* cited by examiner

BIOBASED PEARLESCENT WAXES

CROSS-REFERENCE TO RELATED APPLICATIONS

This is the U.S. national phase of International Application No. PCT/EP2020/054236, filed Feb. 18, 2020, which claims the benefit of European Patent Application No. 19159688.1, filed on Feb. 27, 2019.

FIELD OF THE INVENTION

The invention is in the field of specific waxy esters which in particular in the form of wax dispersions bring about cloudiness and/or pearlescence in cosmetic cleansers. The invention further provides the use of the waxes in cosmetic compositions, the production thereof and the cosmetic compositions themselves.

PRIOR ART

Cosmetic cleansers for skin and/or hair, such as hair shampoos, hair conditioners, shower gels or liquid hand soaps, are usually formulated to be visually appealing. The cosmetic cleansers can be formulated with a glossy mica effect, usually also referred to as pearlescence, or with a non-glossy milky coloration, referred to as cloudiness or white coloration.

As opacifying agent for cosmetic cleansers, finely divided polymer dispersions, usually based on copolymers of (meth) acrylic and styrene, are frequently used. For ecological reasons it is desirable to replace these.

German patent DE19511572 discloses opacifier concentrates based on wax bodies with a hydrophilic and hydrophobic emulsifier. According to this document, ethylene glycol distearate (wax body) in combination with a sugar surfactant (hydrophilic emulsifier) and a monoglyceride (hydrophobic emulsifier) afford low-viscosity, cloudy wax dispersions. The ethylene glycol distearate used is a fatty acid ester based on ethylene glycol prepared by petrochemical means.

Waxes with such a petrochemical basis, such as ethylene glycol monostearate (EGMS) and/or ethylene glycol distearate (EGDS) are also known from the prior art as wax bodies in pearlescent agents and pearlescent concentrates. For instance, a very good pearlescence effect is achieved according to international patent application WO98/38973 by a particularly high C18 fatty acid content or according to international patent application WO2012/177886 by the particular nature of the crystal formation. Furthermore there is extensive prior art enabling conversion of the waxes EDMS and/or EDGS into wax dispersions, for example according to international patent application WO03/066796 by means of nonionic surfactants.

These waxes have to date exclusively been esters of ethylene glycol with a petrochemical basis, i.e. of fossil origin.

The present invention has the object, inter alia, of providing waxes for wax dispersions which enable sustainable human behavior with respect to the environment. Thus, at least the waxes should be fully plant-based and if possible the entire wax dispersion should not be based on petrochemical or fossil raw materials.

At the same time, however, the waxes in the form of their wax dispersions should continue to have at least the same qualities as pearlescent or opacifying agent, if possible even better qualities.

The object has been achieved by waxy esters of ethylene glycol, in particular suitable as an opacifying and/or pearlescent agent in cosmetic cleansers, wherein the ethylene glycol in the ester according to $^{14}C$ analysis has an at least 99% biogenic proportion of carbon, defined according to DIN EN 15440 at 13.6 dpm/gC independently of the matrix, with a standard deviation of +/−0 to +/−4.

Preferably, the ethylene glycol in the ester according to $^{14}C$ analysis has a 100% biogenic proportion of carbon, defined according to DIN EN 15440 at 13.6 dpm/gC independently of the matrix, with a standard deviation of +/−0 to +/−4.

Entirely surprisingly, these waxy esters of ethylene glycol with the biogenic content of $^{14}C$ isotope in the form of a wax dispersion display an improved whiteness compared to the previous esters based on petrochemical or fossil ethylene glycol. This was unexpected since the proportion of $^{14}C$ isotope in the ester of ethylene glycol is extremely low.

In addition, the ethylene glycol esters according to the invention exhibit a lower enthalpy of fusion than comparable petrochemical ethylene glycol esters, meaning that much less energy is required to melt a defined amount of wax of the invention in comparison to the same mass of petrochemical ethylene glycol esters. This enables more economical and energy-efficient production of the wax dispersions and their processibility in cosmetic compositions.

Isotopes are nuclides having the same atomic number (=proton number) but a different number of neutrons present in the nucleus and hence a different mass number [=nucleon number, number of nucleons (protons and neutrons) present in an atomic nucleus]. In addition to the mass, isotopes also differ in angular momentum (nuclear spin), magnetic moment and electric quadrupole moment.

To unambiguously identify the isotopes the (generally conventional for nuclides) notation $^{A}_{Z}X$ is used (X=chemical symbol, A=mass number, Z=atomic number), thus for the stable isotopes of carbon $^{12}_{6}C$; alternatively the notation $^{12}C$ or C-12 is used.

The element carbon has a total of 2 stable isotopes, $^{12}C$ and $^{13}C$. $^{12}C$ has an abundance in nature of about 98.9%, $^{13}C$ of 1.1%. In addition to these two stable isotopes, there are also a number of unstable isotopes. The best-known unstable isotope is $^{14}C$, with a half-life of 5730 years. $^{14}C$ is formed from $^{14}N$ by natural nuclear reaction in the atmosphere: the earth is constantly exposed to cosmic rays, these rays generate free neutrons when they strike the uppermost layers of the earth's atmosphere. In turn, these neutrons react with the nitrogen present in the air in the lower atmosphere at a level of approximately 80%. The following reaction takes place:

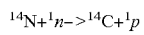

$$^{14}N + {}^{1}n \rightarrow {}^{14}C + {}^{1}p$$

The nucleus of a nitrogen atom with the mass number of 14 (7 neutrons, 7 protons) absorbs a neutron. The radioactive carbon isotope $^{14}C$ (8 neutrons, 6 protons) is formed from the nitrogen atom upon departure of a proton, the mass number thus remains the same. In contrast, $^{12}C$ carbon has 6 neutrons and 6 protons—it is therefore lighter than $^{14}C$.

The $^{14}C$ generated in the atmosphere binds with available oxygen to form carbon dioxide. $^{14}C$ then passes into the biosphere as a result of photosynthesis by plants. Since living beings constantly exchange carbon with the atmosphere during metabolism, the same distribution ratio of the 3 carbon isotopes $^{12}C$, $^{13}C$ and $^{14}C$ is established in living organisms as is present in the atmosphere: Living organisms comprise, per $10^{12}$ stable $^{12}C$ and $^{13}C$ isotopes, approx. 1.2 radioactive $^{14}C$ isotopes.

If carbon is withdrawn from this cycle (i.e. it becomes fossil carbon), this ratio between $^{14}C$ and $^{12}C$ then changes since the decaying $^{14}C$ isotopes are not replaced by new ones.

Fossil fuels such as crude oil, natural gas or coal formed over 100 million years ago, that is to say that these fuels no longer comprise any $^{14}C$ isotopes since the $^{14}C$ isotopes originally present have decayed and no new $^{14}C$ isotopes have been taken up. Accordingly, hydrocarbons originating from fossil sources do not comprises any $^{14}C$ isotopes.

In a preferred embodiment of the invention, the proportion of $^{14}C$ isotopes in relation to the stable $^{12}C$ and $^{13}C$ isotopes is in the range from $6\times10^{-13}$ to $1.2\times10^{-12}$. The reference parameters are all hydrocarbons present in the ethylene glycol.

The $^{14}C$ content of a sample can be determined either by counting the decaying $^{14}C$ isotopes in a Geiger counter (Geiger counter method of Libby), in a liquid scintillation spectrometer or by counting the remaining $^{14}C$ isotopes using accelerator mass spectrometry. Accelerator mass spectrometry (abbreviation: AMS) can be used to detect $^{14}C$ isotopes in the ppt to ppq range (from $10^{-12}$ to $10^{-16}$) in extremely small sample amounts (milligram range) with the aid of nuclear measurement methods. The current 100% biogenic activity is defined for 2018 according to DIN 15440 at 13.6 dpm/gC independently of the matrix.

The esters of ethylene glycol according to the invention can be prepared by esterification of the specific ethylene glycol comprising the $^{14}C$ isotopes. Such ethylene glycol, which is also known under the name "bio-ethylene glycol" or "bio-monoethylene glycol", or else "bio-MEG" for short, is available by various processes. The addition "bio-" refers to the origin of the raw materials from renewable or plant-based raw materials. According to one of the older processes of India Glycols Ind., India, first what is known as "bio-ethanol" is produced from sugarcane or else from sugarcane syrup. From a chemical perspective, bio-ethanol itself is ethyl alcohol. The desired ethylene glycol ("bio-MEG") is produced from bio-ethanol by the India Glycols Ind. process. For this, first ethylene is prepared by catalyzed dehydration (catalyzed elimination of water) and then ethylene oxide is prepared by oxidation, which lastly is converted to bio-MEG by addition of water.

According to a further process, bio-ethanol can be produced anaerobically from sugarcane juice or molasses or bagasse in the presence of yeasts, especially of fungi of the group of sac fungi (ascomycetes), this bio-ethanol being converted to ethene and leading by means of oxidation to vinegar and subsequent hydrogenation to bio-MEG. Bio-MEG produced in this way is also often used to produce so-called PlantBottle™, that is to say PET bottles comprising 30% bio-MEG.

As a result of rising consumption, two additional plants for producing bio-MEG are due to start producing in the near future. According to the announced process of Braskem S. A. and Haldo Topsoe A/S, the MOSAIK™ process (MOno-SAccharide Industrial Cracker) is combined with the Haldor Topsoe™ process so that first sugar is oxidized into smaller molecules and these are converted to ethylene glycol and propylene glycol in the presence of a heterogeneous non-noble metal catalyst.

Avantium Chemicals B.V. plans to produce bio-MEG by the Mekong™ process, the intention being to do this in a single-stage process from mono- and disaccharides with hydrogen in the presence of catalysts and with the elimination of water.

In principle, bio-MEG can also be produced naturally from other renewable raw materials than sugarcane or sugar beet, for example from starchy plants such as cereals, potatoes and corn or from cellulosic raw materials such as straw and wood.

Preference is given to esters of ethylene glycol based on sugarcane or sugar beet, especially in the form of sugar syrup.

Such plant-based ethylene glycols are available for example from India Glycols Ltd, see also http://www.indi-aglycols.com/product_groups/monoethylene_glycol.htm.

The term "ethylene glycol" or monoethylene glycol is ideally understood to mean a 1,2-monoethylene diol following the general formula (I)

$$HOCH_2CH_2OH \qquad (I)$$

In practice, however, chemically produced compounds comprise varying concentrations of byproducts. For the purposes of the invention, preference is given to esters based on ethylene glycol which have a purity of 99.7% to 99.9%, that is to say are 99.7% to 99.9% monoethylene glycol. Particular preference is given to those ethylene glycols which include water in amounts of at most 0.06% by weight and residual catalyst amounts in the ppm range.

The esters according to the invention are preferably produced directly from the fatty acids and plant-based ethylene glycol. Preference is given here to the presence of a catalyst, preferably tin oxalate in amounts of 0.01% to 0.5% by weight based on the mixture. Elevated temperatures, preferably above the melting temperatures of the fatty acids, are advantageous.

For the purposes of the invention, the esters are preferably a mixture of mono- and diester of ethylene glycol, preferably a mixture of 0.5% to 10% by weight, preferably 3% to 10% by weight, of monoester of ethylene glycol and 90% to 99.5% by weight, preferably 90% to 97% by weight, of diester of ethylene glycol.

Ester mixtures of this kind are obtainable through a molar ratio of ethylene glycol:carboxylic acid or fatty acid of preferably 0.9:2 to 1.5:2, in particular 1:2 to 1.1:2.

Examples of suitable carboxylic or fatty acids include fatty acids having 6 to 22 carbon atoms, preferably having 12 to 22 carbon atoms, such as caproic acid, caprylic acid, capric acid, lauric acid, myristic acid, palmitic acid, palm oleic acid, stearic acid, isostearic acid, hydroxystearic acid, oleic acid, elaidic acid, petroselinic acid, linoleic acid, linolenic acid, eleostearic acid, arachic acid, gadoleic acid, behenic acid and erucic acid, and technical-grade mixtures thereof.

Particularly suitable esters are mono- and diesters of ethylene glycol with fatty acids having 6 to 22 carbon atoms, preferably having 12 to 22 carbon atoms and in particular esters of ethylene glycol with a fatty acid mixture consisting of 40% to 100% by weight of stearic acid and
0% to 60% by weight of palmitic acid and
0% to 20% by weight of lauric and/or myristic acid.

According to one embodiment, the invention relates to esters of ethylene glycol and a fatty acid mixture consisting of 85% to 100% by weight of stearic acid and
0% to 15% by weight of palmitic acid and
0% to 15% by weight of lauric and/or myristic acid, the % by weight adding up to 100.

These esters are suitable as opacifying agents and for generating whiteness, preferably in the form of their dispersion in cosmetic compositions.

According to a second embodiment, the invention relates to esters of ethylene glycol and a fatty acid mixture consisting of 40% to 60% by weight of stearic acid and 40% to 60% by weight of palmitic acid and 0% to 20% by weight of lauric and/or myristic acid, the % by weight adding up to 100.

Within this second embodiment, preference is given to those the fatty acid mixture of which consists of 40% to 60% by weight of stearic acid and 40% to 60% by weight of palmitic acid, the % by weight adding up to 100.

Fatty acid mixtures of this kind are commercially available, for example, under the trade name Edenor L2SM®, from KLK Oleo Malaysia.

The esters derived therefrom are suitable for generating pearlescence, preferably in the form of their dispersion in cosmetic compositions.

For the purposes of the present invention, preference is given to esters consisting of 3% to 10% by weight of monoester and 90% to 97% by weight of diester of ethylene glycol of fatty acids or a fatty acid mixture consisting of 40% to 60% by weight of stearic acid and 40% to 60% by weight of palmitic acid.

Preferred ethylene glycol esters have the following characteristics:

acid number AN according to DIN 53402 in the range from 5.5 to 7, especially 6 to 6.5;

hydroxyl number OHN according to DIN 53240 in the range from 5 to 7, especially 5.5 to 6.5;

saponification number SN according to DIN 53401 in the range from 185 to 210, especially 195 to 200.

In the scope of the present invention, the esters described are waxy. In the present application, the term "wax" or "waxy" is understood to refer to a compound which is solid at room temperature, usually kneadable and melts without decomposition. For the purposes of the invention, the melting point is measured on a Kofler hot bench in accordance with ISO 6321 and is preferably above 40° C., preferably below 75° C., and especially between 45° C. and 65° C.

The present invention further provides wax dispersions comprising the ester according to at least one of claims 1 to 6, preferably in amounts of 15% to 30% by weight, with preference in amounts of 20% to 30% by weight, based on the wax dispersion.

The wax dispersions according to the invention preferably additionally comprise surfactants and optionally preservatives.

According to one embodiment, the wax dispersions comprise a) 15% to 30% by weight of esters of ethylene glycol as wax and b) 10% to 30% by weight of surfactants, preferably alkylene oxide-free surfactants c) optionally 0.01% to 1.0% by weight of preservatives.

Surfactants

Surface-active substances (surfactants) may include anionic, nonionic, cationic, amphoteric or zwitterionic surfactants, the proportion of which in the wax dispersions is usually approximately 10% to 30% by weight.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, alk(en)ylpolyglycol ether citrates and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (especially wheat-based plant products) and alkyl (ether) phosphates.

If the anionic surfactants comprise polyglycol ether chains, these may have a conventional homolog distribution, but preferably have a narrowed homolog distribution. Typical examples of particularly suitable mild, i.e. particularly skin-friendly surfactants are fatty alcohol polyglycol ether sulfates such as lauryl ether sulfate having an average degree of ethoxylation of 1 or 2, which for example is available under the trade name Texapon® N70, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, fatty acid glucamides and/or protein fatty acid condensates.

Typical examples of cationic surfactants are quaternary ammonium compounds, such as dimethyl-distearylammonium chloride. Preference is given to ammonium halides, especially chlorides and bromides, such as alkyltrimethylammonium chlorides, dialkyldimethylammonium chlorides and trialkyl-methylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. In addition, the very readily biodegradable quaternary ester compounds, such as, for example, the dialkylammonium methosulfates and methylhydroxyalkyldialkoyloxyalkylammonium methosulfates sold under the trade name Stepantex® and the corresponding products of the Dehyquart® series can be used as cationic surfactants. The term "esterquats" is generally understood to mean quaternized fatty acid triethanolamine ester salts. Particularly preferred cationic surfactants include products known as Dehyquart® L80, Dehyquart® F 75, Dehyquart® A-CA.

Suitable amphoteric or zwitterionic surfactants are alkyl betaines, alkylamido betaines, aminopropionates, aminoglycinates, imidazolinium betaines and sulfobetaines. Examples of suitable alkyl betaines are the carboxyalkylation products of secondary and especially tertiary amines. Typical examples are the carboxymethylation products of hexylmethylamine, hexyldimethylamine, octyldimethylamine, decyldimethylamine, dodecylmethylamine, dodecyldimethylamine, dodecylethylmethylamine, $C_{12/14}$-cocoalkyldimethylamine, myristyldimethylamine, cetyldimethylamine, stearyldimethylamine, stearylethylmethylamine, oleyldimethylamine, $C_{16/18}$-tallowalkyldimethylamine and also the technical-grade mixtures thereof. Also useful, in addition, are carboxyalkylation products of amido amines. Typical examples are reaction products of fatty acids having 6 to 22 carbon atoms, namely caproic acid, caprylic acid, capric acid, lauric acid, myristic acid, palmitic acid, palm oleic acid, stearic acid, isostearic acid, oleic acid, elaidic acid, petroselinic acid, linoleic acid, linolenic acid, eleostearic acid, arachic acid, gadoleic acid, behenic acid and erucic acid, and the technical-grade mixtures thereof, with N,N-dimethylaminoethylamine, N,N-dimethylaminopropylamine, N,N-diethylaminoethylamine and N,N-diethylaminopropylamine, which are condensed with sodium chloroacetate. Very particular preference is given to what is known as cocamidopropyl betaine, which is commercially available under the trade name Dehyton® PK 45.

Furthermore, imidazolinium betaines are also suitable. These substances are also known substances which can be obtained for example by cyclizing condensation of 1 or 2 mol of fatty acid with polyfunctional amines, for example aminoethylethanolamine (AEEA) or diethylenetriamine. The corresponding carboxyalkylation products are mixtures of different open-chain betaines. Typical examples are condensation products of the abovementioned fatty acids with AEEA, preferably imidazolines based on lauric acid or again $C_{12/14}$-coconut fatty acid which are subsequently betainized with sodium chloroacetate.

Typical examples of nonionic surfactants are fatty alcohol (poly)glycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, partially oxidized alk(en)yl oligoglycosides and glucuronic acid derivatives, fatty acid N-alkylglucamides, polyol fatty acid esters, sugar esters, sorbitan esters, polysorbates and amine oxides. If the nonionic surfactants comprise polyglycol ether chains, these may have a conventional homolog distribution, but preferably have a narrowed homolog distribution. Examples of suitable nonionic surfactants are ethoxylated fatty alcohols, for example a fatty alcohol ethoxylated with 4 mol of ethylene oxide or an ethoxylated fatty alcohol mixture with C12/C14 proportions such as the commercially available Dehydol® LS4.

Preference is given, among the nonionic surfactants, in particular for mild preparations, to alkyl and/or alkenyl oligoglycosides of the formula (II)

$$RO\text{-}[G]_p \qquad (II)$$

in which R is an alkyl and/or alkenyl radical having 4 to 22 carbon atoms, G is a sugar radical having 5 or 6 carbon atoms and p is numbers from 1 to 10. They can be obtained by the relevant methods of preparative organic chemistry. The alkyl and/or alkenyl oligoglycosides can be derived from aldoses or ketoses having 5 or 6 carbon atoms, preferably from glucose. The preferred alkyl and/or alkenyl oligoglycosides are therefore alkyl and/or alkenyl oligoglucosides. The index number p specifies the degree of oligomerization (DP), i.e. the distribution of mono- and oligoglycosides and is a number between 1 and 10. Whereas p in a given compound must always be an integer and can here in particular assume the values p=1 to 6, the value p for a particular alkyl oligoglycoside is an analytically determined calculated parameter which in most cases is a fraction. Preference is given to using alkyl and/or alkenyl oligoglycosides having a mean degree of oligomerization p of 1.1 to 3.0. From a technical applications perspective, preference is given to those alkyl and/or alkenyl oligoglycosides for which the degree of oligomerization is less than 1.7 and is especially between 1.2 and 1.4.

The alkyl or alkenyl radical R can be derived from primary alcohols having 4 to 11, preferably 8 to 10 carbon atoms. Typical examples are butanol, caproic alcohol, caprylic alcohol, capric alcohol and undecyl alcohol, and also their technical-grade mixtures, as obtained, for example, in the hydrogenation of technical-grade fatty acid methyl esters or during the hydrogenation of aldehydes from Roelen's oxo synthesis. Preference is given to alkyl oligoglucosides having a chain length of $C_8$-$C_{10}$ (DP=1 to 3), which are obtained as forerun in the distillative separation of technical-grade $C_8$-$C_{18}$ coconut fatty alcohol, and may be contaminated with a fraction of less than 6% by weight $C_{12}$ alcohol, and also alkyl oligoglucosides based on technical-grade $C_{9/11}$ oxo alcohols (DP=1 to 3). The alkyl or alkenyl radical R can further also be derived from primary alcohols having 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and also the technical-grade mixtures thereof which may be obtained as described above. Preference is given to alkyl oligoglucosides based on hydrogenated $C_{12/14}$ coconut alcohol with a DP of 1 to 3.

Particularly preferred nonionic surfactants include a mixture of alkylpolyglucosides composed of $C_{12}$-alkyl glucoside and $C_{8-10}$-alkyl glucoside in a ratio by weight of 1.5:1 to 2.5:1, based on active substance.

Particularly preferably, the surfactants present in the wax dispersions are nonionic surfactants and the wax dispersions preferably comprise a) 15% to 30% by weight of esters of ethylene glycol as wax and
b) 10% to 30% by weight of nonionic surfactants, preferably selected from the group made up of alkyl and/or alkylene polyglucosides, and
c) optionally 0.01% to 0.5% by weight of preservatives.

Excellent white cloudiness/pearlescence is obtained when the wax dispersions comprise a) 15% to 30% by weight of esters of ethylene glycol as wax consisting of a1) 3% to 10% by weight of monoester of ethylene glycol and a2) 90% to 97% by weight of diester of ethylene glycol, and
b) 10% to 30% by weight of nonionic surfactants selected from the group made up of alkyl and/or alkylene polyglucosides, and
c) optionally 0.01% to 0.5% by weight of preservatives.

Within this group, wax dispersions comprising a) 15% to 30% by weight of esters of ethylene glycol as wax consisting of 3% to 10% by weight of monoester and 90% to 97% by weight of diester of ethylene glycol with a mixture of fatty acids composed of 40% to 60% by weight of stearic acid and 40% to 60% by weight of palmitic acid and
b) 10% to 30% by weight of nonionic surfactants selected from the group made up of alkyl and/or alkylene polyglucosides, and
c) optionally 0.01% to 0.5% by weight of preservatives and in particular wax dispersions comprising
a) 15% to 30% by weight of esters of ethylene glycol as wax consisting of 3% to 10% by weight of monoester and 90% to 97% by weight of diester of ethylene glycol with a mixture of fatty acids composed of 40% to 60% by weight of stearic acid and 40% to 60% by weight of palmitic acid and
b) 10% to 30% by weight of a mixture of alkyl polyglucosides composed of $C_{12}$-alkyl glucoside and $C_{8-10}$-alkyl glucoside in a ratio by weight of 1.5:1 to 2.5:1, based on active substance, and
c) optionally 0.01% to 0.5% by weight of preservatives, are advantageous.

Examples of suitable preservatives which may be present are citric acid and benzoic acid and/or salts thereof, phenoxyethanol, formaldehyde solution, parabens, pentanediol, sorbic acid, levulinic acid and arachidonic acid, and also the silver complexes known under the Surfacine® name, and the additional substance classes listed in Annex 6, parts A and B, of the Cosmetics Directive. Citric acid and benzoic acid and/or salts thereof, such as Na salts, are particularly suitable.

The wax dispersions according to the invention always comprise water ad 100% by weight.

In the context of the invention, the wax dispersions comprise minimal amounts, preferably between 0% and 10% by weight, of petrochemical compounds, and especially no petrochemical compounds, based on the wax dispersion. Thus, the preferred active ingredients of the wax dispersions are to be based as fully as possible, preferably between 90% and 100% by weight and especially completely, based on the wax dispersion, on renewable raw materials.

The present invention further provides for the use of the esters of the invention according to at least one of claims 1 to 6 as wax, preferably in the form of its dispersion of the invention according to any of claims 7 to 13, for generating cloudiness or pearlescence in aqueous media, preferably for generating cloudiness or pearlescence in cosmetic compositions for cleansing skin and/or hair.

The waxes according to the invention are preferably used in the form of the wax dispersions of the invention according to any one of claims 7 to 13.

Cosmetic Composition

The present invention further provides cosmetic cleansers for skin and hair comprising an ester of ethylene glycol according to claim 1 as a pearlescent or opacifying agent.

Cosmetic compositions for cleansing hair are to be understood as meaning rinse-out compositions. Cosmetic compositions for cleansing hair are understood to be all cosmetic hair treatment compositions which are intended for the sole cleansing of the hair and also those which are intended for the care, drying, color alteration or structural alteration of the hair and include a cleansing step. For example, this is intended to include hair shampoos, hair conditioners, conditioning shampoos, hair rinses, hair treatments, hair masks, hair tonics, permanent wave fixing solutions, hair coloring shampoos, hair colorants or combinations thereof.

Cosmetic compositions for cleansing the skin are understood to be compositions which free the skin surface of dirt and grease and optionally provide care to the skin, for example shower gels, shower baths, shower oils, foam baths, liquid hand soaps, intimate wash lotions, face cleansing lotions.

Depending on the intended use, these preparations comprise a series of further auxiliaries and additives, such as further surfactants, oil bodies, emulsifiers, cosurfactants, (cationic) polymers, bodying agents, thickeners, superfatting agents, stabilizers, silicone compounds, fats, waxes, lecithins, phospholipids, UV light protection factors, biogenic active ingredients, antioxidants, antidandruff agents, film formers, swelling agents, tyrosine inhibitors (depigmenting agents), hydrotropes, solubilizers, preservatives, perfume oils, dyes, and the like.

In the cosmetic compositions according to the invention, the waxes are advantageously present in the form of a dispersion, preferably in amounts of 0.1 to 5.0, preferably in amounts of 0.2% to 2.5% by weight, and especially 0.3% to 2.0% by weight, based on the content of ester of ethylene glycol.

Suitable further ingredients for the use according to the invention and for the cosmetic compositions according to the invention are given hereinafter.

Surfactants

In the context of the present invention, the cosmetic compositions can comprise anionic, nonionic, cationic and amphoteric or zwitterionic surfactants. The choice of surfactants depends on the intended use. Suitable surfactants have already been listed by way of example in connection with the surfactants of the wax dispersion according to the invention in the context of this application. These examples are also suitable as further surfactants for the cosmetic compositions. In addition to the wax dispersions according to the invention, cosmetic compositions for conditioning hair treatment typically comprise anionic surfactants.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, alk(en)ylpolyglycol ether citrates and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (especially wheat-based plant products) and alkyl (ether) phosphates. If the anionic surfactants comprise polyglycol ether chains, these may have a conventional homolog distribution, but preferably have a narrowed homolog distribution. The anionic surfactants used are particularly preferably the fatty alcohol (ether sulfates) that have already been described in association with the wax dispersions of the invention, and especially lauryl ether sulfate with 1 or 2 mol of ethylene oxide.

In addition to the wax dispersions according to the invention and the anionic surfactants, the cosmetic compositions for conditioning hair treatment preferably also comprise amphoteric or zwitterionic surfactants. Suitable amphoteric or zwitterionic surfactants are alkyl betaines, alkylamido betaines, aminopropionates, aminoglycinates, imidazolinium betaines and sulfobetaines. Examples of suitable alkyl betaines are the carboxyalkylation products of secondary and especially tertiary amines. Typical examples are the carboxymethylation products of hexylmethylamine, hexyldimethylamine, octyldimethylamine, decyldimethylamine, dodecylmethylamine, dodecyldimethylamine, dodecylethylmethylamine, $C_{12/14}$-cocoalkyldimethylamine, myristyldimethylamine, cetyldimethylamine, stearyldimethylamine, stearylethylmethylamine, oleyldimethylamine, $C_{16/18}$-tallowalkyldimethylamine and also the technical-grade mixtures thereof. Also useful, in addition, are carboxyalkylation products of amido amines. Typical examples are reaction products of fatty acids having 6 to 22 carbon atoms, namely caproic acid, caprylic acid, capric acid, lauric acid, myristic acid, palmitic acid, palm oleic acid, stearic acid, isostearic acid, oleic acid, elaidic acid, petroselinic acid, linoleic acid, linolenic acid, eleostearic acid, arachic acid, gadoleic acid, behenic acid and erucic acid, and the technical-grade mixtures thereof, with N,N-dimethylaminoethylamine, N,N-dimethylaminopropylamine, N,N-diethylaminoethylamine and N,N-diethylaminopropylamine, which are condensed with sodium chloroacetate. Very particular preference is given to what is known as cocamidopropyl betaine, which is commercially available under the trade name Dehyton® PK 45.

Oil Bodies

Useful oil bodies are, for example, Guerbet alcohols based on fatty alcohols having 6 to 18, preferably 8 to 10, carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$ fatty acids with branched alcohols, especially 2-ethylhexanol, esters of $C_{18}$-$C_{38}$-alkylhydroxycarboxylic acids with linear or branched $C_6$-$C_{22}$ fatty alcohols, especially dioctyl malate, esters of linear and/or branched fatty acids with polyhydric alcohols (e.g. propylene glycol, dimer diol or trimer triol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, especially benzoic acid, esters of $C_2$-$C_{12}$ dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$ fatty alcohol carbonates, e.g. dicaprylyl carbonate (Cetiol® CC), Guerbet carbonates based on fatty alcohols having 6 to 18, preferably 8 to 10 carbon atoms, esters of benzoic acid with linear and/or branched $C_6$-$C_{22}$ alcohols (e.g. Finsolv® TN), linear or branched, symmetrical or asymmetrical dialkyl ethers having 6 to 22 carbon atoms per alkyl group, such as dicaprylyl ether (Cetiol® OE), ring-opening products of epoxidized fatty acid esters with polyols, silicone oils (cyclic dimethicones, referred to as (INCI) cyclomethicones, polymethylsiloxanes, referred to as (INCI) dimethicones, amino-functional silicones, referred to as (INCI) amodimethicones such as trimethylsilylamodimethicones, inter alia) and/or aliphatic or naphthenic hydrocarbons such as squalane, squalene, or dialkylcyclohexanes. Suitable silicone oils are described in European patent EP1830798 on pages 8-14, to which reference is hereby expressly made.

Emulsifiers

Suitable emulsifiers are, for example, nonionogenic surfactants from at least one of the following groups:
  addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and alkylamines having 8 to 22 carbon atoms in the alkyl radical;
  addition products of 1 to 15 mol of ethylene oxide onto castor oil and/or hydrogenated castor oil;
  addition products of 15 to 60 mol of ethylene oxide onto castor oil and/or hydrogenated castor oil;
  adducts having 1 to 30 mol of ethylene oxide onto partial esters of glycerol and/or sorbitan with unsaturated, linear or saturated, branched fatty acids having 12 to 22 carbon atoms and/or hydroxycarboxylic acids having 3 to 18 carbon atoms;
  partial esters of polyglycerol (average degree of self-condensation 2 to 8), polyethylene glycol (molecular weight 400 to 5000), sorbitan, trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and adducts thereof having 1 to 30 mol of ethylene oxide;
  mixed esters of pentaerythritol, fatty acids, citric acid and fatty alcohol and/or mixed esters of fatty acids having 6 to 22 carbon atoms, methylglucose and polyols, preferably glycerol or polyglycerol;
  mono-, di- and trialkyl phosphates, and mono-, di- and/or tri-PEG-alkyl phosphates and salts thereof;
  wool wax alcohols;
  polysiloxane-polyalkyl-polyether copolymers and corresponding derivatives;
  block copolymers, for example polyethyleneglycol-30 dipolyhydroxystearates;
  polymer emulsifiers, for example Pemulen grades (TR-1, TR-2) from Goodrich;
  polyalkylene glycols and
  glycerol carbonate.

Particularly preferred emulsifiers are addition products of ethylene oxide onto $C_{12118}$ fatty acid mono- and diesters, addition products of 1 to 30, preferably 5 to 10 mol, of ethylene oxide onto hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric diglyceride, malic acid monoglyceride, malic acid diglyceride, and the technical-grade mixtures thereof. Addition products of 1 to 30 mol, preferably 5 to 10 mol, of ethylene oxide onto sorbitan esters are likewise suitable. Useful sorbitan esters include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan tri ricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and the technical-grade mixtures thereof. Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate and mixtures thereof. Examples of further suitable polyol esters are the mono-, diand triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like. Preference is also given to trimethylpropane EO/PO trioleate, a mixture obtainable by the reaction of trimethylolpropane trioleate with ethylene oxide and propylene oxide under alkaline conditions. Here, ethylene oxide units (EO) and propylene oxide units (PO) are incorporated, at least in part, into the ester groups of the trimethylolpropane trioleate. The trimethylpropane EO/PO trioleate is characterized by the statistical average of its content of EO and PO units per molecule. In one embodiment of the present invention, trimethylpropane EO/PO trioleate having 120 ethylene oxide units (EO) and 10 propylene oxide units (PO) is used.

Partial glycerides are mono and/or diesters of glycerol with linear, saturated and/or partially unsaturated fatty acids, for example, caproic acid, caprylic acid, capric acid, lauric acid, myristic acid, palmitic acid, palm oleic acid, tallow fatty acid, stearic acid, behenic acid and technical-grade mixtures thereof. They have the formula (III),

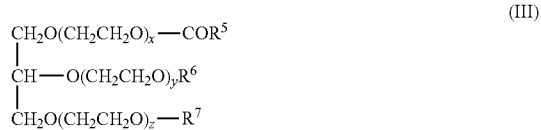

in which $R^5CO$ is an acyl radical having 6 to 22 carbon atoms, preferably a linear, saturated acyl radical having 6 to 22 carbon atoms, $R^6$ and $R^7$ are each independently hydrogen or $R^5CO$, x, y and z in total are 0 or numbers from 1 to 30 and X is an alkali metal or alkaline earth metal, with the proviso that at least one of the two radicals $R^6$ and $R^7$ is hydrogen. Typical examples are lauric acid monoglyceride, lauric acid diglyceride, coconut fatty acid monoglyceride, coconut fatty acid triglyceride, palmitic acid monoglyceride, palmitic acid triglyceride, stearic acid monoglyceride, stearic acid diglyceride, tallow fatty acid monoglyceride, tallow fatty acid diglyceride, behenic acid monoglyceride, behenic acid diglyceride and technical-grade mixtures thereof which may still comprise minor amounts of triglyceride from the production process.

Also suitable as wax bodies as a preferred group are esters of polybasic, optionally hydroxy-substituted carboxylic acids with fatty alcohols having 6 to 22 carbon atoms. Suitable acid components of these esters are, for example, malonic acid, maleic acid, fumaric acid, adipic acid, sebacic acid, azelaic acid, dodecanedioic acid, phthalic acid, isophthalic acid and, in particular, succinic acid and also malic acid, citric acid and in particular tartaric acid and mixtures thereof. The fatty alcohols comprise 6 to 22, preferably 12 to 18 and especially 16 to 18 carbon atoms in the alkyl chain. Typical examples are caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, eleostearyl alcohol, arachyl alcohol, gadoleyl alcohol, behenyl alcohol, erucyl alcohol and brassidyl alcohol and technical-grade mixtures thereof. The esters may be present as full or partial esters, preference being given to using monoesters and especially diesters of carboxylic acids or hydroxycarboxylic acids. Typical examples are succinic acid mono- and dilauryl esters, succinic acid mono- and dicetearyl esters, succinic acid mono- and distearyl esters, tartaric acid mono- and dilauryl esters, tartaric acid mono- and dicocoalkyl esters, tartaric acid mono- and dicetearyl esters, citric acid mono, di- and trilauryl esters, citric acid mono-, di- and tricocoalkyl esters and citric acid mono-, di- and tricetearyl esters.

As a third preferred group of wax bodies, use may be made of fatty alcohols having the formula (IV),

in which $R^8$ is a linear, optionally hydroxy-substituted alkyl radical and/or acyl radical having 16 to 48, preferably 18 to 36 carbon atoms. Typical examples of suitable alcohols are cetearyl alcohol, hydroxystearyl alcohol, behenyl alcohol and oxidation products of long-chain paraffins.

Fatty ketones, which are suitable as components, preferably have the formula (V),

in which $R^9$ and $R^{10}$ are each independently alkyl and/or alkenyl radicals having 1 to 22 carbon atoms, with the proviso that they have in total at least 24 and preferably 32 to 48 carbon atoms. The ketones may be prepared by prior-art processes, for example by pyrolysis of the corresponding fatty acid magnesium salts. The ketones may be symmetrical or asymmetrical in structure; preferably, however, the two radicals $R^{13}$ and $R^{14}$ differ only by one carbon atom and are derived from fatty acids having 16 to 22 carbon atoms.

Fatty aldehydes suitable as wax bodies preferably correspond to the formula (VI),

in which $R^{11}CO$ is a linear or branched acyl radical having 24 to 48, preferably 28 to 32 carbon atoms.

Likewise suitable are fatty ethers preferably of the formula (VII),

in which $R^{12}$ and $R^{13}$ are each independently alkyl and/or alkenyl radicals having 1 to 22 carbon atoms, with the proviso that they have in total at least 24 and preferably 32 to 48 carbon atoms. Fatty ethers of the type mentioned are typically prepared by acidic condensation of the corresponding fatty alcohols. Fatty ethers with particularly advantageous pearlescent properties are obtained by condensation of fatty alcohols having 16 to 22 carbon atoms such as cetyl alcohol, cetearyl alcohol, stearyl alcohol, isostearyl alcohol, oleyl alcohol, behenyl alcohol and/or erucyl alcohol.

Also suitable as a component are fatty carbonates, preferably of formula (VIII),

in which $R^{14}$ and $R^{15}$ are each independently alkyl and/or alkenyl radicals having 1 to 22 carbon atoms, with the proviso that they have in total at least 24 and preferably 32 to 48 carbon atoms. The substances are obtained by transesterifying, for example, dimethyl carbonate or diethyl carbonate with the corresponding fatty alcohols in a manner known per se. Accordingly, the fatty carbonates may be symmetrical or asymmetrical in structure. However, preference is given to using carbonates in which $R^{14}$ and $R^{15}$ are identical and are alkyl radicals having 16 to 22 carbon atoms. Particular preference is given to transesterification products of dimethyl carbonate or diethyl carbonate with cetyl alcohol, cetearyl alcohol, stearyl alcohol, isostearyl alcohol, oleyl alcohol, behenyl alcohol and/or erucyl alcohol in the form of their mono- and diesters or technical-grade mixtures thereof.

Epoxide ring-opening products are known substances which are customarily prepared by acid-catalyzed reaction of terminal or internal olefin epoxides with aliphatic alcohols. The reaction products preferably have the formula (IX),

in which $R^{16}$ and $R^{17}$ are hydrogen or an alkyl radical having 10 to 20 carbon atoms, with the proviso that the sum total of carbon atoms of $R^{16}$ and $R^{17}$ is in the range from 10 to 20 and $R^{18}$ is an alkyl and/or alkenyl radical having 12 to 22 carbon atoms and/or the radical of a polyol having 2 to 15 carbon atoms and 2 to 10 hydroxyl groups. Typical examples are ring-opening products of α-dodecene epoxide, α-hexadecene epoxide, α-octadecene epoxide, α-eicosene epoxide, α-docosene epoxide, i-dodecene epoxide, i-hexadecene epoxide, i-octadecene epoxide, i-eicosene epoxide and/or i-docosene epoxide with lauryl alcohol, coconut fatty alcohol, myristyl alcohol, cetyl alcohol, cetearyl alcohol, stearyl alcohol, isostearyl alcohol, oleyl alcohol, elaidyl alcohol, petroselinyl alcohol, linolyl alcohol, linolenyl alcohol, behenyl alcohol and/or erucyl alcohol. Preference is given to using ring-opening products of hexadecene and/or octadecene epoxides with fatty alcohols having 16 to 18 carbon atoms. If polyols are used for the ring opening instead of fatty alcohols, they are, for example, the following substances: glycerol; alkylene glycols such as ethylene glycol, diethylene glycol, propylene glycol, butylene glycol, hexylene glycol and polyethylene glycols having an average molecular weight of 100 to 1000 daltons; technical-grade oligoglycerol mixtures having a degree of self-condensation of 1.5 to 10 such as technical-grade diglycerol mixtures having a diglycerol content of 40% to 50% by weight; methylol compounds such as, in particular, trimethylolethane, trimethylolpropane, trimethylolbutane, pentaerythritol and dipentaerythritol; lower alkyl glucosides particularly those having 1 to 8 carbon atoms in the alkyl radical such as methyl glucoside and butyl glucoside; sugar alcohols having 5 to 12 carbon atoms such as sorbitol or mannitol, sugars having 5 to 12 carbon atoms such as glucose or sucrose; amino sugars such as glucamine.

Bodying Agents and Thickeners

Suitable bodying agents are primarily fatty alcohols or hydroxy fatty alcohols having 12 to 22 and preferably 16 to 18 carbon atoms and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are for example Aerosil grades (hydrophilic silicas), polysaccharides, especially xanthan gum, guar gum, agar agar, alginates and tyloses, carboxymethylcellulose, hydroxyethylcellulose and hydroxypropylcellulose, further higher molecular-weight polyethylene glycol monoesters and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Particularly effective substances have also been found to be bentonites, for example Bentone® Gel VS-5PC (Rheox), which is a mixture of cyclopentasiloxane, distearidimonium hectorite and propylene carbonate. Also useful are surfactants, for example ethoxylated fatty acid glycerides, esters of fatty acids with polyols, for example pentaerythritol or trimethylolpropane, fatty alcohol ethoxylates with a narrowed homolog distribution or alkyl oligoglucosides, and electrolytes, such as sodium chloride and ammonium chloride.

Superfatting Agents

Examples of superfatting agents which may be used include substances such as lanolin and lecithin, and polyethoxylated or acylated lanolin and lecithin derivatives, polyol fatty acid esters, monoglycerides and fatty acid alkanolamides, the latter simultaneously serving as foam stabilizers.

Stabilizers

Stabilizers used may be metal salts of fatty acids, for example magnesium stearate or ricinoleate, aluminum stearate or ricinoleate and/or zinc stearate or ricinoleate.

(Cationic) Polymers

In addition to the wax dispersions according to the invention, the anionic surfactants and optionally amphoteric or zwitterionic surfactants, the cosmetic compositions for conditioning hair treatment preferably also comprise cationic polymers. Suitable cationic polymers are preferably those from the group of cationically modified cellulose derivatives, PQ 10, PQ 67, cationically modified guar derivatives, such as Dehyquart® Guar N, guar hydroxypropyltrimonium chloride, cationic homo- or copolymers based on acrylamide, cationic homo- or copolymers based on vinylpyrrolidone, cationic homo- or copolymers based on quaternized vinylimidazole and cationic homo- or copolymers based on methacrylates.

Suitable cationic polymers are, for example, quaternized hydroxyethylcellulose, also obtainable under the name Polymer JR 400® from Amerchol, cationic starch, copolymers of diallylammonium salts and acrylamides, quaternized vinylpyrrolidone/vinylimidazole polymers, such as Luviquat® (BASF), condensation products of polyglycols and amines, quaternized protein hydrolyzates, polypeptides and amino acids, for example laurydimonium hydroxypropyl hydrolyzed collagen (Lamequat® L/Grünau), quaternized wheat polypeptides, polyethyleneimine, cationic silicone polymers such as, for example, amidomethicones, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides such as, for example, described in FR-A 2252840 and also the cross-linked water-soluble polymers thereof, cationic chitin derivatives such as quaternized chitosan, optionally in microcrystalline distribution, condensation products of dihaloalkyls, such as, for example, dibromobutane with bisdialkylamines, such as, for example, bisdimethylamino-1,3-propane, cationic guar gum such as, for example, Jaguar® CBS, Jaguar® C-17, Jaguar® C-16 from Celanese, quaternized ammonium salt polymers such as, for example, Mirapol® A-15, Mirapol® AD-1, Mirapol® AZ-1 from Miranol. Especially suitable cationic polymers are polyquaternium-68, obtainable as Luviquat® Supreme AT 1, or polyquaternium-11, obtainable as Luviquat® PQ 11 AT 1.

Useful anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers and optionally derivatized cellulose ethers and silicones.

Silicone Compounds

Suitable silicone compounds are, for example, dimethylpolysiloxanes, methylphenylpolysiloxanes, cyclic silicones, and amino-, fatty acid-, alcohol-, polyether-, epoxy-, fluorine-, glycoside- and/or alkyl-modified silicone compounds, which at room temperature may be either liquid or else in the form of a resin. Also suitable are simethicones, which are mixtures of dimethicones with an average chain length of from 200 to 300 dimethylsiloxane units and hydrogenated silicates.

UV Light Protection Filters

UV light protection factors are understood to mean, for example, organic substances (light protection filters) which are liquid or crystalline at room temperature and which are capable of absorbing ultraviolet rays and of re-releasing the energy absorbed in the form of radiation of longer wavelength, for example heat. UVB filters can be oil-soluble or water-soluble. Examples of oil-soluble substances are:

- 3-benzylidenecamphor or 3-benzylidenenorcamphor and derivatives thereof, e.g. 3-(4-methylbenzylidene)camphor described;
- 4-aminobenzoic acid derivatives, preferably 2-ethylhexyl 4-(dimethylamino)benzoate, 2-octyl 4-(dimethylamino)benzoate and amyl 4-(dimethylamino)benzoate;
- esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);
- esters of salicylic acid, preferably 2-ethylhexyl salicylate, 4-isopropylbenzyl salicylate, homomenthyl salicylate;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably di-2-ethylhexyl 4-methoxybenzmalonate;
- triazine derivatives, for example 2,4,6-trianilino-(p-carbo-2'-ethyl-1'-hexyloxy)-1,3,5-triazine and Octyl Triazone or Dioctyl Butamido Triazone (Uvasorb® HEB);
- propane-1,3-diones, for example 1-(4-tert-butylphenyl)-3-(4'-methoxyphenyl)propane-1,3-dione;
- ketotricyclo(5.2.1.0)decane derivatives.

Suitable water-soluble substances are:

- 2-phenylbenzimidazole-5-sulfonic acid and the alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidenecamphor, for example 4-(2-oxo-3-bornylidenemethyl)benzenesulfonic acid and 2-methyl-5-(2-oxo-3-bornylidene)sulfonic acid and salts thereof.

Suitable typical UVA filters are especially derivatives of benzoylmethane, for example 1-(4'-tertbutylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds. The UVA and UVB filters can of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Combinations of this type are advantageously combined with water-soluble filters, for example 2-phenylbenzimidazole-5-sulfonic acid and the alkali metal, alkaline earth metal, ammonium, alkylammonium, alkanolammonium and glucammonium salts thereof.

In addition to the soluble substances mentioned, insoluble light protection pigments, specifically finely dispersed metal oxides and salts, are also useful for this purpose. Examples of suitable metal oxides are especially zinc oxide and titanium dioxide, and additionally oxides of iron, of zirconium, of silicon, of manganese, of aluminum and of cerium, and mixtures thereof. The salts used may be silicates (talc), barium sulfate or zinc stearate. The oxides and salts are used in the form of the pigments for skincare and skin-protecting emulsions and decorative cosmetics. Here, the particles should have an average diameter of less than 100 nm, preferably between 5 and 50 nm and in particular between 15 and 30 nm. They may have a spherical shape, but it is also possible to use those particles which have an ellipsoidal shape or a shape which deviates in some other way from the spherical configuration. The pigments may also be in surface-treated form, i.e. hydrophilized or hydrophobized. Typical examples are coated titanium dioxides, for example titanium dioxide T 805 (Degussa) or Eusolex® T2000 (Merck). Suitable hydrophobic coating agents are in particular silicones and specifically trialkoxyoctylsilanes or simethicones. In sunscreen compositions, preference is given to using so-called micropigments or nanopigments. Preference is given to using micronized zinc oxide.

Biogenic Active Ingredients and Antioxidants

Biogenic active ingredients are understood to mean, for example, tocopherol, tocopherol acetate, tocopherol palmitate, ascorbic acid, (deoxy)ribonucleic acid and the fragmentation products thereof, β-glucans, retinol, bisabolol, allantoin, phytantriol, panthenol, AHA acids, amino acids, ceramides, pseudoceramides, essential oils, plant extracts, for example Prunus extract, bambara nut extract or vitamin complexes.

Antioxidants interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. α-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids), suitable in accordance with the invention, of these specified active ingredients.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof and similar compounds.

Antidandruff Active Ingredients

Useful antidandruff active ingredients include piroctone olamine (1-hydroxy-4-methyl-6-(2,4,4-trimythylpentyl)-2-(1H)-pyridinone monoethanolamine salt), Baypival® (climbazole), Ketoconazole®, (4-acetyl-1-1-{-4-[2-(2,4-dichlorophenyl)r-2-(1H-imidazol-1-ylmethyl)-1,3-dioxylan-c-4-ylmethoxyphenyl}piperazine, ketoconazole, Elubiol, selenium disulfide, colloidal sulfur, sulfur polyethylene glycol sorbitan monooleate, sulfur ricinol polyethoxylate, sulfur tar distillates, salicylic acid (and/or in combination with hexachlorophene), undecylenic acid monoethanolamide sulfosuccinate sodium salt, Lamepon® UD (protein-undecylenic acid condensate), zinc pyrithione, aluminum pyrithione and magnesium pyrithione/dipyrithione-magnesium sulfate.

Further Additives

Swelling agents for aqueous phases which may be used are montmorillonites, clay mineral substances, pemulen and alkyl-modified Carbopol grades (Goodrich). Further suitable polymers and swelling agents can be found in the overview by R. Lochhead in Cosm. Toil. 108, 95 (1993). Suitable insect repellents are N,N-diethyl-m-toluamide, 1,2-pentanediol or ethyl butylacetylaminopropionate, and a suitable self-tanning agent is dihydroxyacetone. Suitable tyrosine inhibitors, which prevent the formation of melanin and are applied in depigmenting agents, are, for example, arbutin, ferulic acid, kojic acid, coumaric acid and ascorbic acid (vitamin C).

Protein Hydrolyzates

If desired, further protein hydrolyzates known from the prior art may be used, for example based on keratin such as the commercially available Nutrilan® Keratin W PP, or based on wheat, such as Gluadin® WLM Benz, Gluadin® WK or Gluadin® WP. It is also possible to add small amounts of free amino acids such as lysine or arginine.

Hydrotropes

Flow behavior may also be improved by using hydrotropes, for example ethanol, isopropyl alcohol or polyols. Polyols which are suitable here preferably have 2 to 15 carbon atoms and at least two hydroxyl groups. The polyols may comprise still other functional groups, in particular amino groups, or be modified with nitrogen. Typical examples are glycerol;

alkylene glycols, for example ethylene glycol, diethylene glycol, propylene glycol, butylene glycol, hexylene glycol, and polyethylene glycols with an average molecular weight of from 100 to 1000 daltons;

technical-grade oligoglycerol mixtures with a degree of self-condensation of from 1.5 to 10, for example technical-grade diglycerol mixtures with a diglycerol content of 40% to 50% by weight;

methylol compounds, such as especially trimethylolethane, trimethylolpropane, trimethylolbutane, pentaerythritol and dipentaerythritol;

lower alkyl glucosides, especially those with 1 to 8 carbon atoms in the alkyl radical, for example methyl and butyl glucoside;

sugar alcohols having 5 to 12 carbon atoms, for example sorbitol or mannitol;

sugars having 5 to 12 carbon atoms, for example glucose or sucrose;

amino sugars, for example glucamine;

dialcoholamines such as diethanolamine or 2-amino-1,3-propanediol.

Preservatives

Examples of suitable preservatives are benzoates, phenoxyethanol, formaldehyde solution, parabens, pentanediol, sorbic acid, levulinic acid and arachidonic acid, and also the silver complexes known under the Surfacine® name, and the additional substance classes listed in Annex 6, parts A and B, of the Cosmetics Directive.

Perfume Oils and Aromas

Mention may be made, as perfume oils, of mixtures of natural and synthetic fragrances. Natural fragrances are extracts from flowers (lily, lavender, rose, jasmine, neroli, ylang ylang), stems and leaves (geranium, patchouli, petitgrain), fruits (aniseed, coriander, caraway, juniper), fruit peels (bergamot, lemon, orange), roots (mace, angelica, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, aisomethylionone and methyl cedryl ketone, the alcohols include anethole, citronellol, eugenol, isoeugenol, geraniol, linalool, phenylethyl alcohol and terpineol, and the hydrocarbons include primarily the terpenes and balsams. However, preference is given to using mixtures of different fragrances which together produce a pleasant scent note. Essential oils of relatively low volatility, which are mostly used as aroma components, are also suitable as perfume oils, e.g. sage oil, chamomile oil, clove oil, melissa oil, mint oil, cinnamon leaf oil, linden blossom oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzyl acetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, Iso-ESuper, Fixolide NP, evernyl, iraldein gamma, phenylacetic acid, geranyl acetate, benzyl acetate, rose oxide, romillate, irotyl and floramate alone or in mixtures. Examples of suitable aromas include peppermint oil, spearmint oil, aniseed oil, star anise oil, caraway oil, eucalyptus oil, fennel oil, lemon oil, wintergreen oil, clove oil, menthol and the like.

Dyes

Dyes which can be used are the substances approved and suitable for cosmetic purposes, as listed, for example, in the publication "Kosmetische Farbemittel" [Cosmetic Colorants] from the Farbstoffkommission der Deutschen Forschungsgemeinschaft [Dyes Commission of the German Research Society], Verlag Chemie, Weinheim, 1984, pp. 81-106. Examples are cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). As a luminescent dye, it is also possible for luminol to be present. These dyes are usually used in concentrations of from 0.001% to 0.1% by weight, based on the total mixture.

Pigments

In particular in the form of their wax dispersions, the esters according to the invention can produce outstanding white cloudiness in the cosmetic compositions. If the desire is to enhance pearlescence further, it is possible to add pigments.

The term pigment encompasses particles of any kind which are white or colored, organic or inorganic, are insoluble in the preparations, and serve the purpose of imparting increased luster on the preparation.

Of advantage are the luster pigments, which, according to DIN 55944: 2003-11, include the metal effect pigments and the pearlescent pigments.

Some specific effect pigments cannot be assigned to these two groups, for example graphite platelets, iron oxide platelets and micronized titanium dioxide, micronized titanium dioxide not giving a luster effect, but rather an angle-dependent light-scattering effect. The luster pigments according to DIN 55943: 2001-10 are predominantly effect pigment platelets. Aligned in parallel, luster pigments exhibit a characteristic luster. The visual effect of luster pigments is based on the directed reflection on metallic particles (metal effect pigments), on transparent particles with a high refractive index (pearlescent pigments) or on the phenomenon of interference (interference pigments) (DIN 55944: 2003-11).

Examples of commercial effect pigments preferred in accordance with the invention are: Timiron® and #174; from Merck, Iriodin® and #174; from Merck (pearlescent and color luster pigments for decorative industrial applications), Xirallic® and #174; from Merck (intense-color crystal effect pigments).

The pigments can also be used in the form of commercially available oily or aqueous predispersions.

Cosmetic Hair Treatment Compositions

In a particular embodiment of the present invention, cosmetic compositions for conditioning hair treatment are claimed, comprising the wax dispersions of the invention, anionic surfactants and optionally cationic polymers, and optionally amphoteric and/or zwitterionic surfactants and emulsifiers or further customary ingredients, and also water for supplementation to 100% by weight.

The following are preferably present in the conditioning hair treatment compositions—based on active substance content:

0.1% to 5.0% by weight, preferably 0.2% to 2.5% by weight, of wax dispersion of the invention, 1.0% to 15% by weight, preferably 7.5% to 12% by weight, of anionic surfactants, 0.0% to 1% by weight, preferably 0.05% to 0.4% by weight, of at least one cationically modified polymer and/or 0.0% to 15% by weight, preferably 0.1% to 5% by weight, of amphoteric and/or zwitterionic surfactants, 0.0% to 10% by weight of emulsifiers and optionally further customary ingredients may be present, and water for supplementation to 100% by weight.

The wax dispersion, anionic surfactants, and the optionally present cationic polymers and amphoteric and/or zwitterionic surfactants, and the optional further customary ingredients, have already been described above in this application.

Process

The present invention further provides a process for the production of the cosmetic cleansers according to the invention. According to one of the processes of the invention, the waxy esters of ethylene glycol of the invention are added in the form of the wax dispersion preferably to one or more initially charged constituents of the cosmetic compositions at room temperature, preferably between 15 and 30° C., and are stirred in particular using a commercial stirrer—what is known as the cold process.

According to a further process variant, the cosmetic compositions can be produced by heating the esters of ethylene glycol of the invention to temperatures above their melting point and stirring them with at least one of the remaining constituents of the cosmetic compositions. The waxy ester of ethylene glycol is preferably heated to temperatures above the melting point of the ester of the invention together with a further constituent, this being solid at room temperature, of the cosmetic composition and stirred, before the further remaining constituents of the cosmetic composition are then added and stirred.

EXAMPLES

A) Preparation Examples for Ethylene Glycol Distearate of the Invention

Inventive Example A1

A mixture of 2172.5 g (=35 mol) of plant-based ethylene glycol (indices: at least 99.8% by weight monoethylene glycol and at most 0.06 diethylene glycol; at most 0.06% by weight water; commercially available from India Glycols Bio MEG) and 19 913.6 g (=70 mol) of technical-grade stearic acid (composition $C_{16}$ fatty acid:$C_{18}$ fatty acid=1:1; commercially available as Palmera B1804® from KLK Oleo) and 11 g of tin oxalate (esterification catalyst, commercially available as Fascate® 2001 from PMC Organometallix, Inc.) was heated to 160° C. About 80% of the theoretical amount of water was distilled off within 16 hours.

The mixture was then heated to 240° C. and the remaining amount of water removed within 26 hours.

For the workup, the product was stirred with an NaOH solution (184.6 g dissolved in 500 g of deionized water) for 30 minutes at 80° C., filtered and dried.

This afforded 14 998 g of a white, solid product with the following characteristics:

Acid number AN according to DIN 53402=1.6

Hydroxyl number OHN according to DIN 53240=4.7

Saponification number SN according to DIN 53401=196.2

Melting point on Kofler hot bench=63.2° C.

Comparative Example Ethylene Glycol Distearate A2 (not According to the Invention)

Serving as comparison was an ethylene glycol distearate prepared from petrochemical ethylene glycol (indices: at least 99.9% by weight monoethylene glycol and at most 0.05 diethylene glycol; at most 0.05% by weight water) having the following characteristics:

Acid number AN according to DIN 53402<1

Hydroxyl number OHN according to DIN 53240<15

Melting point on Kofler hot bench=63.2° C.

commercially available, for example, as Cutina® AGS, BASF Personal Care & Nutrition GmbH.

The current 100% biogenic activity, i.e. biogenic proportion of $^{14}C$ carbon in % is defined for 2018 according to DIN at 13.6 dpm/gC, independently of the matrix.

The ethylene glycol distearate of the invention prepared according to example 1 and the petrochemical ethylene glycol distearate according to the comparative example have the following $^{14}C$ contents (8 measurements):

| | % $^{14}C$ | Carbon chain distribution $C_{16}$ and $C_{18}$ | GC % by weight | |
|---|---|---|---|---|
| | % $^{14}C$ | C16 C18 | Monoester | Diester |
| Of the invention according to A1 | 100 | 44.4: 52.5 | 0.9 | 98.8 |
| Comparison A2 | 98 | 48-52: 48-52 | 8 | 92 |
| Ethylene glycol as basis for A1 | 100 | Not present, as there is no ester | — | — |

B) Production of the Wax Dispersions/Pearlescent Concentrates

The following pearlescent concentrates/wax dispersions were produced (table 1). The amounts are given in % by weight of active substance AS, based on the wax dispersion/pearlescent concentrate.

To produce the wax dispersion, ⅔ of the total amount of water was initially charged and heated to 85° C. Ethylene glycol distearate (of the invention or comparison) and the alkyl polyglucosides were stirred into the hot phase in succession. At 64° C., the last ⅓ of the total amount of water was added and the mixture was stirred. From 40° C., Na benzoate, Na sulfate and citric acid were added and stirred.

TABLE 1

Wax dispersions

| Composition (INCI) | B1 | Comparison B2 |
|---|---|---|
| Wax body Ethylene glycol distearate of the invention according to A1 | 22.5 | — |
| Wax body Ethylene glycol distearate according to comparison A2 | — | 22.5 |
| Lauryl glucoside* Plantacare 1200 ® | 19 | 19 |
| C8/C10-alkyl glucoside* Glucopon 215 UP ® | 8.3 | 8.3 |
| Benzoic acid | 0.5 | 0.5 |
| Citric acid 50% | 12.4 | 12.4 |
| Water | ad 100 | ad 100 |
| pH | 4.7 | 4.7 |
| Viscosity | 8800 | 12 360 |
| Viscosity after thickening at 40° C. | 12 120 | 18 200 |
| Appearance whiteness | + | 0 |
| Appearance pearlescence | + | 0 |

*Amount based on active substance

Viscosity was determined by the Brookfield method (23° C., spindle 5, 10 rpm, mPas).

The whiteness/pearlescence was ascertained visually by naked eye by comparison with one another.

As can be seen from table 1, the wax dispersion with the plant-based ethylene glycol difatty acid ester A1 of the invention exhibits better whiteness/pearlescence and a lower viscosity compared to the wax dispersion with the petrochemical-based ethylene glycol distearate A2.

C) Production of Further Wax Dispersions/Pearlescent Concentrates

Further pearlescent concentrates/wax dispersions were produced according to table 2. The amounts are given in % by weight of active substance AS, based on the wax dispersion/pearlescent concentrate.

To produce the wax dispersion, water, ethylene glycol distearate (according to the invention) and the surfactants laureth-4 (C12 fatty alcohol ethoxylated with an average of 4 mol of ethylene oxide), cocamidopropyl betaine and sodium laureth sulfate (Na salt of a C12 ether sulfate ethoxylated with an average of 1 ethylene oxide) and Na benzoate were heated to 85° C. with stirring at approx. 50 rpm. The dispersion is allowed to cool to 25° C. with stirring at approx. 50 rpm. Citric acid was then added and the mixture was stirred.

TABLE 2

Wax dispersions C1-C4

| Composition (INCI) | C1 | C2 | C3 | C4 |
|---|---|---|---|---|
| Wax body Ethylene glycol distearate of the invention according to A1 | 20 | 26 | 18 | 20 |
| Surfactant Laureth-4 | 5 | 12 | — | — |
| Surfactant Cocamidopropyl betaine | — | 8 | 2 | 20 |
| Surfactant Sodium laureth-1 sulfate | — | — | 20 | — |
| Na benzoate | 0.5 | 0.5 | 0.5 | 0.5 |
| Citric acid 50% | 0.8 | 0.8 | 0.8 | 0.8 |
| Water | ad 100 | ad 100 | | |
| pH (10% in water) | 4.5 | 4.2 | 4.4 | 4.2 |
| Viscosity in mPas; Brookfield RVT, spindle 4/10 rpm | 2500 | 8000 | 3500 | 3000 |

TABLE 2-continued

| Wax dispersions C1-C4 | | | | |
|---|---|---|---|---|
| Composition (INCI) | C1 | C2 | C3 | C4 |
| Appearance whiteness | + | + | + | + |
| Appearance pearlescence | + | + | + | + |

D) Production of a Hair Shampoo with Wax Dispersion B1)

To produce the hair shampoo, water was initially charged at room temperature in accordance with table 3, and guar hydroxypropyltrimonium chloride (thickener) was scattered in and dispersed. The surfactants laureth-4 (C12 fatty alcohol ethoxylated with an average of 4 mol of ethylene oxide) and cocamidopropyl betaine were dissolved therein. The wax dispersion from example B1) and the further constituents were then added and the mixture was stirred. The amounts in table 3 are in % by weight, the % by weight for the wax dispersion relating to the wax dispersion of B1) and the % by weight for the surfactants relating to the active substance content AS.

TABLE 3

| Hair shampoo D1) | |
|---|---|
| Composition (INCI) | D1 |
| Water | 82.5 |
| Surfactant Sodium laureth-1 sulfate | 10.0 |
| Surfactant Cocamidopropyl betaine | 2.0 |
| Guar hydroxypropyltrimonium chloride | 0.2 |
| Wax dispersion B1) | 2 |
| Na benzoate | 0.5 |
| Citric acid 50% | 0.3 |
| Sodium chloride | 2.0 |
| Perfume | 0.3 |
| pH (10% in water) | 4.8 |
| Viscosity in mPas; Brookfield RVT, spindle 4/10 rpm | 10 000 |
| Appearance whiteness | + |
| Appearance pearlescence | + |

The invention claimed is:

1. Waxy esters of ethylene glycol suitable as an opacifying and/or pearlescent agent in cosmetic cleansers, wherein the ethylene glycol in the ester according to $^{14}$C analysis has an at least 99% biogenic proportion of carbon, defined according to DIN EN 15440 at 13.6 dpm/gC independently of the matrix, with a standard deviation of +/−0 to +/−4;
   wherein the waxy esters of ethylene glycol comprise a mixture of a monoester and a diester of ethylene glycol.

2. The waxy esters of ethylene glycol according to claim 1, wherein the ethylene glycol in the ester according to $^{14}$C analysis has a 100% biogenic proportion of carbon, defined according to DIN EN 15440 at 13.6 dpm/gC independently of the matrix, with a standard deviation of +/−0 to +/−4.

3. The waxy esters of ethylene glycol according to claim 1, comprising the monoester or the diesters of ethylene glycol with fatty acids having 6 to 22 carbon atoms.

4. The waxy esters of ethylene glycol according to claim 1 comprising mono-and diesters of ethylene glycol with fatty acid mixtures consisting of
   40% to 100% by weight of stearic acid and
   0% to 60% by weight of palmitic acid and
   0% to 20% by weight of lauric and/or myristic acid.

5. The waxy esters of ethylene glycol according to claim 1 consisting of 3% to 10% by weight of monoester and 90% to 97% by weight of diester of ethylene glycol of a mixture of fatty acids consisting of 40% to 60% by weight of stearic acid and 40% to 60% by weight of palmitic acid.

6. A wax dispersion comprising a waxy ester of ethylene glycol according to claim 1 in an amount of 15% to 30% by weight, based on the wax dispersion.

7. The wax dispersion according to claim 6, comprising a) 15% to 30% by weight of an ester of ethylene glycol as wax and b) 10% to 30% by weight of surfactant, and c) optionally 0.01% to 1.0% by weight of preservatives.

8. The wax dispersion according to claim 6 comprising a) 15% to 30% by weight of an ester of ethylene glycol as wax, b) 10% to 30% by weight of a nonionic surfactant, and c) optionally 0.01% to 0.5% by weight of preservatives.

9. The wax dispersion according to claim 6 comprising
   a) 15% to 30% by weight of an ester of ethylene glycol as wax consisting of a1) 3% to 10% by weight of monoester of ethylene glycol and a2) 90% to 97% by weight of diester of ethylene glycol, and
   b) 10% to 30% by weight of a nonionic surfactant selected from the group consisting of alkyl and/or alkylene polyglucosides, and
   c) optionally 0.01% to 0.5% by weight of preservatives.

10. The wax dispersion according to claim 6 comprising
    a) 15% to 30% by weight of an ester of ethylene glycol as wax consisting of 3% to 10% by weight of monoester and 90% to 97% by weight of diester of ethylene glycol with a mixture of fatty acids composed of 40% to 60% by weight of stearic acid and 40% to 60% by weight of palmitic acid and
    b) 10% to 30% by weight of a nonionic surfactant selected from the group consisting of alkyl and/or alkylene polyglucosides, and
    c) optionally 0.01% to 0.5% by weight of preservatives.

11. The wax dispersion according to claim 6, wherein the wax dispersion is free of petrochemical compounds.

12. The wax dispersion according to claim 6, wherein the esters of ethylene glycol have a melting point above 40° C.

13. A cosmetic cleanser for skin and hair comprising an ester of ethylene glycol according to claim 1 as a pearlescent or opacifying agent.

14. A process for the production of a cosmetic cleanser, wherein an ester of ethylene glycol according to claim 1, in the form of a dispersion at room temperature, is added with stirring to one or more initially charged constituents of the cosmetic composition.

15. A process for the production of a cosmetic cleanser, wherein an ester of ethylene glycol according to claim 1 is heated to temperatures above the melting point and stirred with at least one of the remaining constituents of the cosmetic composition.

16. The waxy ester of ethylene glycol according to claim 3 wherein the fatty acid has 2 to 12 carbon atoms.

17. The wax dispersion of claim 7 wherein the surfactant is an alkylene oxide-free surfactant.

18. The wax dispersion of claim 8 wherein the nonionic surfactant is selected from the group consisting of alkyl and/or alkylene polyglucosides.

19. The wax dispersion according to claim 12 wherein the esters of ethylene glycol have a melting point below 75° C.

20. The waxy esters of ethylene glycol according to claim 1, wherein the mixture contains 0.5% to 10% by weight of monoester of ethylene glycol and 90% to 99.5% by weight of diester of ethylene glycol.

21. The waxy esters of ethylene glycol according to claim 1, wherein the mixture contains 3% to 10% by weight of monoester of ethylene glycol and 90% to 97% by weight of diester of ethylene glycol.

22. The waxy esters of ethylene glycol according to claim 1, wherein the mixture is obtained through a molar ratio of ethylene glycol: carboxylic acid or fatty acid of preferably 0.9:2 to 1.5:2.

* * * * *